(12) United States Patent
Gifford et al.

(10) Patent No.: US 7,520,172 B2
(45) Date of Patent: Apr. 21, 2009

(54) INSPECTION SYSTEM FOR INSPECTING A STRUCTURE AND ASSOCIATED METHOD

(75) Inventors: Carl B. Gifford, Buckley, WA (US); Jeffrey R. Kollgaard, Kent, WA (US)

(73) Assignee: The Boeing Company, Chicago, IL (US)

( * ) Notice: Subject to any disclaimer, the term of this patent is extended or adjusted under 35 U.S.C. 154(b) by 530 days.

(21) Appl. No.: 11/221,048

(22) Filed: Sep. 7, 2005

(65) Prior Publication Data

US 2007/0051177 A1    Mar. 8, 2007

(51) Int. Cl.
*G01N 29/24* (2006.01)
*G01N 29/26* (2006.01)
*G01N 29/06* (2006.01)
*G01N 29/04* (2006.01)

(52) U.S. Cl. .............................. 73/599; 73/602; 73/631; 73/642

(58) Field of Classification Search .................. 73/1.82, 73/1.86
See application file for complete search history.

(56) References Cited

U.S. PATENT DOCUMENTS

| | | | | |
|---|---|---|---|---|
| 2,984,756 A | * | 5/1961 | Bradfield | 310/327 |
| 4,068,524 A | * | 1/1978 | Lewis et al. | 73/614 |
| 4,327,588 A | * | 5/1982 | North | 73/599 |
| 4,577,505 A | * | 3/1986 | Jestrich et al. | 73/629 |
| 4,769,793 A | | 9/1988 | Kniest et al. | |
| 5,095,754 A | * | 3/1992 | Hsu et al. | 73/602 |
| 5,349,860 A | | 9/1994 | Nakano et al. | |
| 5,553,499 A | * | 9/1996 | Hisata et al. | 73/606 |
| 5,952,578 A | * | 9/1999 | White | 73/622 |
| 5,974,886 A | * | 11/1999 | Carroll et al. | 73/598 |
| 6,070,466 A | | 6/2000 | Taran et al. | |
| 6,182,512 B1 | | 2/2001 | Lorraine | |
| 6,234,025 B1 | | 5/2001 | Gieske et al. | |
| 6,476,541 B1 | | 11/2002 | Smith et al. | |
| 6,495,833 B1 | | 12/2002 | Alfano et al. | |
| 6,552,841 B1 | * | 4/2003 | Lasser et al. | 359/305 |
| 6,810,743 B2 | | 11/2004 | Madaras et al. | |
| 6,853,926 B2 | | 2/2005 | Alfano et al. | |
| 2004/0051035 A1 | | 3/2004 | Zombo et al. | |
| 2005/0098728 A1 | | 5/2005 | Alfano et al. | |
| 2006/0213273 A1 | * | 9/2006 | Lasser et al. | 73/606 |

OTHER PUBLICATIONS

UK Search Report from Great Britain Patent Application No. 0806187.1.

* cited by examiner

*Primary Examiner*—Hezron Williams
*Assistant Examiner*—Rose M Miller
(74) *Attorney, Agent, or Firm*—Alston & Bird LLP

(57) ABSTRACT

A system and method for inspecting a structure having a coating on at least one surface are provided. The system includes at least one ultrasonic sensor positioned proximate to the structure. Each sensor is capable of transmitting a shear wave toward the structure and receiving return signals in response thereto, wherein the shear wave includes at least one reference beam and at least one interrogating beam. The system further includes a data acquisition system in communication with the sensor for generating information indicative of the coating based on at least one return signal associated with the reference beam.

21 Claims, 7 Drawing Sheets

INSPECTION SYSTEM FOR INSPECTING A STRUCTURE AND ASSOCIATED METHOD

BACKGROUND OF THE INVENTION

1) Field of the Invention

The present invention relates to non-destructive inspection and, more particularly, to non-destructive inspection of a structure for defects using an inspection system in conjunction with a data acquisition system.

2) Description of Related Art

It is frequently desirable to inspect structures to identify defects or flaws, such as cracks, discontinuities, voids, or porosity, which could adversely affect the performance of the structure. Non-destructive inspection ("NDI") of structures is typically utilized to thoroughly examine a structure without harming the structure or requiring significant disassembly. Non-destructive inspection is typically preferred to avoid the schedule, labor, and costs associated with removal of a part for inspection, as well as avoidance of the potential for damaging the structure. NDI is advantageous for many applications in which a thorough inspection of the exterior and/or interior of a structure is required. For example, NDI is commonly used in the aircraft industry to inspect aircraft structures for any type of internal or external damage to, or defects (flaws) in, the structure. Inspection may be performed during manufacturing or after the completed structure has been put into service, including field testing, to validate the integrity and fitness of the structure.

Various types of sensors may be used to perform NDI. One or more sensors may move over the portion of the structure to be examined, and receive data regarding the structure. For example, a pulse-echo (PE), through-transmission (TT), or shear-wave sensor may be used to obtain ultrasonic data, such as for thickness gauging, detection of laminar defects and porosity, and/or crack detection in the structure. Resonance, pulse-echo, or mechanical impedance sensors are typically used to provide indications of voids or porosity, such as in adhesive bondlines of the structure. High resolution inspection of aircraft structure is commonly performed using ultrasonic testing (UT) to provide a plan view image of the part or structure under inspection. Data acquired by sensors is typically processed and then presented to a user via a display as a graph of amplitude of the received signal. To increase the rate at which the inspection of a structure is conducted, a scanning system may include arrays of inspection sensors, i.e., arrays of transmitters and/or detectors.

Various coatings, such as paint, primer, adhesive layers, or corrosion inhibiting compounds, may be applied to metallic structures, complicating NDI of the structures. Generally, NDI techniques used on thicker structures are incompatible and unreliable for inspecting thinner structures having coatings. Thin materials may have relatively small flaws that would be acceptable in a thicker structure but that have a disproportionately large affect on the quality of a thin structure and, therefore, are desirably detected. With the detection of such smaller flaws, more noise and other spurious signals are also detected and analyzed which can lead to false results and render the NDI technique unreliable. Moreover, the complications upon NDI posed by a coating are also generally more pronounced with respect to thinner structures.

Generally, a robust NDI technique has an acceptable signal-to-noise ratio (i.e., 3-to-1) and is capable of identifying flaws, at least larger flaws, rather than spurious signals. However, a robust NDI technique may miss some smaller flaws since the signals generated by the smaller flaws may be considered noise. A sensitive NDI technique has a lower signal-to-noise ratio so as to identify smaller flaws, but is more prone to identify spurious signals as being indicative of a potential flaw since the spurious signals will sometimes exceed the signal threshold that has been established to define a flaw. Adding gain to a sensitive NDI technique in an attempt to detect smaller flaws amplifies spurious signals, as well as flaws, which leads to false rejections of structures. Conversely, reducing gain to a sensitive NDI technique provides a more robust inspection because less false signals will be identified to be indicative of flaws, but the inspection is less sensitive and not as many flaws, especially smaller flaws, will be identified.

Previous NDI techniques determined the attenuation of the worst case coating condition, generally the thickest possible coating of the most attenuative material, and compensated for the attenuation by adding gain. However, in practice this often leads to excessive gain settings on a structure that does not have the worst case coating condition. Excessive gain settings to offset attenuation created by a coating magnify the noise level, causing irrelevant signals to be mistaken for defects, particularly for thinner structures. As such, unwarranted repairs and a loss of confidence in the inspection technique may result. Moreover, paint stripping of the structure prior to an inspection due to the difficulty in inspecting thinly coated metallic structures has been an expensive alternative. However, without a reliable inspection system, this may be one of the few alternatives for inspecting the coated structure.

One type of NDI uses ultrasonic shear wave techniques. However, NDI using ultrasonic shear wave techniques causes several problems when inspecting thin structures having a coating applied thereon. The coating dampens the ultrasonic beam entering the structure as the ultrasonic beam bounces between opposing surfaces of the structure, which attenuates the ultrasonic energy until there is insufficient ultrasonic energy to detect flaws. In addition, ultrasonic shear waves entering the structure can convert to less well-behaved modes resulting in unpredictability in locating flaws within the structure. Moreover, modifying the coating thickness generates nonlinear attenuation effects (i.e., no change, small change, or large change in attenuation) such that modeling these effects is difficult. Without an accurate model, it is more difficult to use a gain compensation formula as would otherwise be employed by ultrasonic inspection techniques to account for coating thickness variations. Such a formula would also require a priori knowledge of the coating thickness on the structure to be tested, which is generally not known.

It would therefore be advantageous to provide an inspection system that is more reliable for inspecting thin structures having a coating. It would also be advantageous to provide an inspection system that is capable of compensating for attenuation and adjusting gain to compensate for a coating present on the structure. It would be further advantageous to provide an inspection system that is practical and economical.

BRIEF SUMMARY OF THE INVENTION

Embodiments of the present invention address the above needs and achieve other advantages by providing an inspection system for inspecting, among other structures, thin metallic structures having a coating. The inspection system employs one or more ultrasonic sensors for transmitting a shear wave towards the structure. The shear wave typically includes an interrogating beam and a reference beam that propagates through or reflects off of the surface of the structure. A data acquisition system is capable of generating attenuation information indicative of the coating based on a return signal associated with the reference beam. Based on the attenuation information, the gain of the sensor may be adjusted to compensate for the attenuation effects caused by the coating. Therefore, the inspection system is capable of more reliably characterizing a flaw within the structure.

In one embodiment of the present invention, a system for inspecting a structure having a coating on at least one surface is provided. The system includes at least one ultrasonic sensor positioned proximate to the structure. Each sensor is capable of transmitting a shear wave toward the structure and receiving return signals in response thereto, wherein the shear wave includes a reference beam and/or an interrogating beam. The system further includes a data acquisition system in communication with the sensor for generating information indicative of the coating based on a return signal associated with the reference beam.

In various aspects of the present invention, the system includes a device positioned adjacent to the structure for orienting the shear wave generated by the sensor relative to the structure. The device could be a wedge having at least one angular surface, wherein the angular surface is positioned adjacent to the structure. The device could also be an angled reflection mirror attached to a tuning fork. In addition, an array of ultrasonic sensors may be employed, wherein each sensor is capable of transmitting a shear wave toward the structure at an orientation defined by the device. The device may also include a mirror positioned substantially perpendicular to an angle defined between the interrogating beam and the reference beam. The mirror may be positioned to reflect the reference beam back to the sensor. In additional aspects of the present invention, a beam splitter is capable of splitting the shear wave into the reference beam and interrogating beam. The system may include a second ultrasonic sensor that is capable of receiving a return signal associated with the reference beam that provides attenuation information.

Furthermore, the data acquisition system is capable of characterizing a flaw within the structure based on a return signal associated with the interrogating beam. The data acquisition system is also capable of generating attenuation information based on the return signal associated with the reference beam. In addition, the data acquisition system is capable of applying a gain to a return signal associated with the interrogating beam based on the attenuation information so that flaws may be properly identified and characterized.

Further aspects of the system include at least one ultrasonic interrogating sensor positioned adjacent to the structure, wherein the interrogating sensor is capable of transmitting an interrogating beam through the structure and receiving a return signal associated with the interrogating beam in response. The system could also include a plurality of ultrasonic reference sensors positioned adjacent to the structure, wherein the reference sensors include a transmitting sensor capable of transmitting a reference beam through the structure and a receiving sensor capable of receiving a return signal associated with the reference beam transmitted by the transmitting sensor. Additionally, the system includes a data acquisition system capable of communicating with each of the interrogating and reference sensors such that the data acquisition system generates information indicative of the coating based on the return signal received by the receiving sensor. The transmitting sensor and the receiving sensor may be separated by approximately twice a distance between the interrogating sensor and the flaw. However, the interrogating and reference sensors may also be configured to transmit the interrogating and reference beams, respectively, at a frequency and angle that are substantially the same.

Embodiments of the present invention also provide a method for inspecting a structure having a coating on at least one surface. The method includes transmitting an ultrasonic reference beam and an ultrasonic interrogating beam towards the structure, and acquiring at least one return signal from the reference beam that is indicative of the coating. The method also includes generating attenuation information based on the return signal associated with the reference beam, and adjusting a gain to be applied to a return signal associated with the interrogating beam based on the attenuation information.

In various aspects of the method of present invention, the method further includes generating information indicative of at least a portion of the structure based on the return signal associated with the interrogating beam, and characterizing a flaw within the structure based thereupon. The transmitting step may include separately transmitting each of the interrogating and reference beams with respective ultrasonic sensors, or splitting a shear wave into the reference beam and interrogating beam. Moreover, the method could include comparing the attenuation information to a calibration standard prior to adjusting the gain to be applied to a return signal associated with the interrogating beam.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
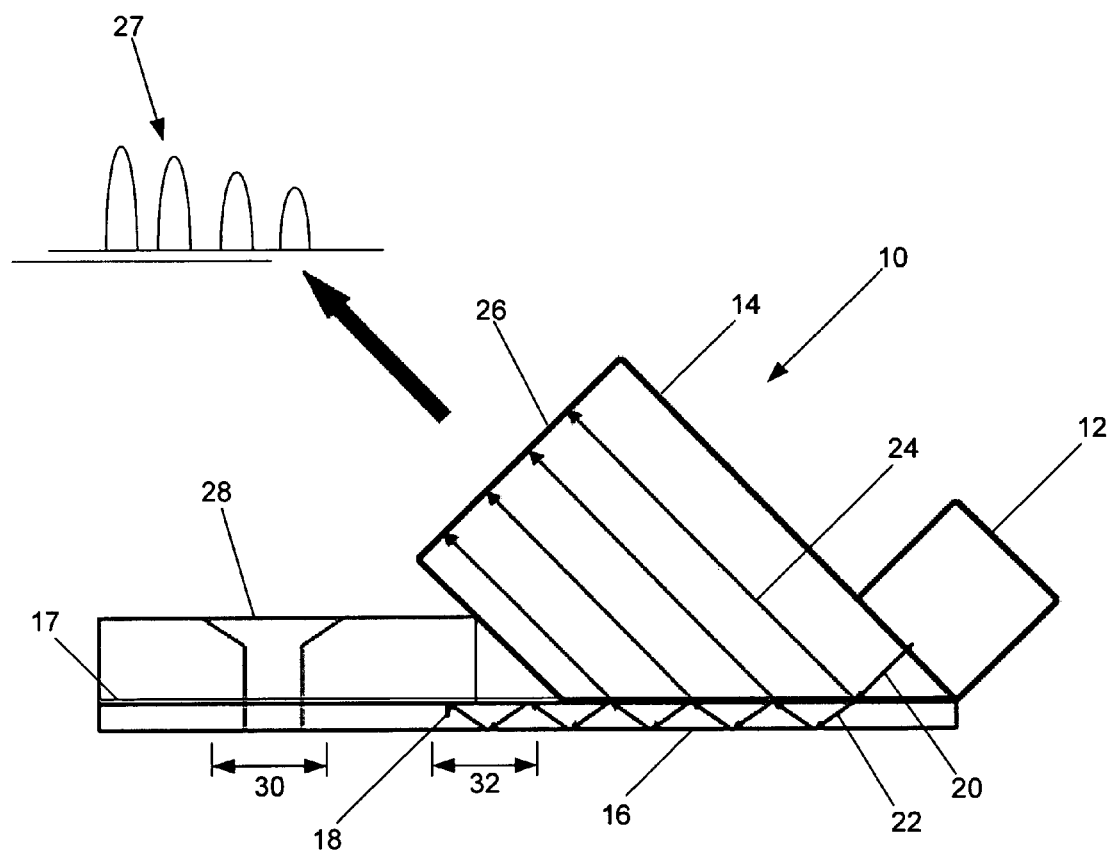
FIG. 1 is an elevation view of an inspection system including a wedge and ultrasonic mirror according to one embodiment of the present invention.

Referring now to the drawings and, in particular to FIG. 1, there is shown an inspection system 10 for inspecting a coated metallic structure 16. The inspection system 10 includes an ultrasonic sensor 12 that is, in one embodiment, carried by a wedge 14 and is in communication with a data acquisition system. As the sensor 12 transmits a shear wave within and through the structure 16, data returning from the structure is sent to the data acquisition system for processing. Typically, the wedge 14 is moved manually along the surface of the structure 16 such that the sensor 12 acquires information regarding the attenuation caused by the presence of the coating on the structure. However, the wedge 14 could be moved in an automated fashion if desired. In addition, the sensor 12 is capable of acquiring information indicative of the remainder of the structure 16, such as to characterize a flaw 18 within the structure. The gain of the sensor 12 may be adjusted according to embodiments of the present invention based on the attenuation information such that the sensor is able to account for attenuation to more reliably identify and characterize the flaw 18.

The inspection system 10 could be used to inspect any number of structures in a variety of industries where detection of flaws or defects in the structure is required or desired, such as in the aircraft, automotive, or construction industries. The sensor 12 is capable of detecting any number of flaws within or along the surface of the structure, such cracks, disbonds, discontinuities, voids, or porosity, which could adversely affect the performance of the structure. More specifically, with reference to the aircraft industry, the sensor 12 is capable of detecting scribe line cracks, cracks in pressure bulkhead webs, cracks in the lower row rivets at lap splices, and cracks beneath repair doublers.

The term "structure" is not meant to be limiting, as the inspection system 10 could be used to inspect any number of thin parts or structures of different shapes and sizes, such as machined forgings, castings, or panels. The inspection could be performed on newly manufactured structures or existing structures that are being inspected for preventative maintenance purposes. Further, the structure 16 could be any number of metallic materials, such as aluminum. While the inspection system and method of embodiments of the present invention will be described principally in conjunction with the inspection of thin, coated structures, the inspection system and method may also inspect other structures, such as thicker structures. As also used herein, "thin" is not meant to be limiting, as the structure 16 could be various thicknesses, but is typically less than 100 mil in thickness. For example, aircraft paneling is a thin metallic structure capable of being inspected by the inspection system 10 of embodiments of the present invention.

A coating is applied to at least one surface of the structure 16. There could be various types of coatings applied to at least one surface of the structure 16, such as paint, primer, adhesive layers, or corrosion-inhibiting compounds. The coating could range in thickness, for example, from about 0.5 to 20 mil.

The sensor 12 could be any suitable ultrasonic sensor or transducer capable of generating information for inspecting a structure 16, and could be attached to the wedge 14 or other carrier or housing using any suitable technique, such as with various fasteners or adhesives. Thus, the sensor 12 is typically a non-destructive sensor, such that the sensor is capable of inspecting a structure 16 without harming the structure or requiring disassembly of the structure. The sensor 18 could be also be configured as an array transducer, such as a linear array transducer, including, for example, phased array transducers as known to those skilled in the art. As shown in FIG. 1, there is a single sensor 12 for acquiring both attenuation information and information for characterizing a flaw 18. However, there may be dedicated sensors 12 for acquiring respective attenuation information and information for characterizing a flaw, if desired.

Figure 2A:
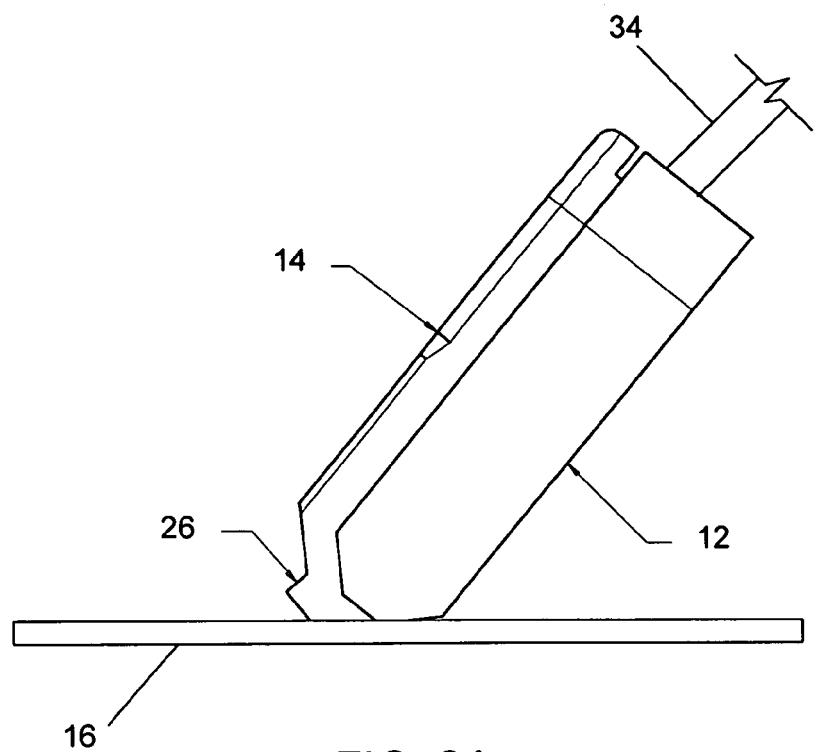
FIG. 2A is an elevation view of an inspection system including a wedge and ultrasonic mirror according to another embodiment of the present invention.
Figure 2B:
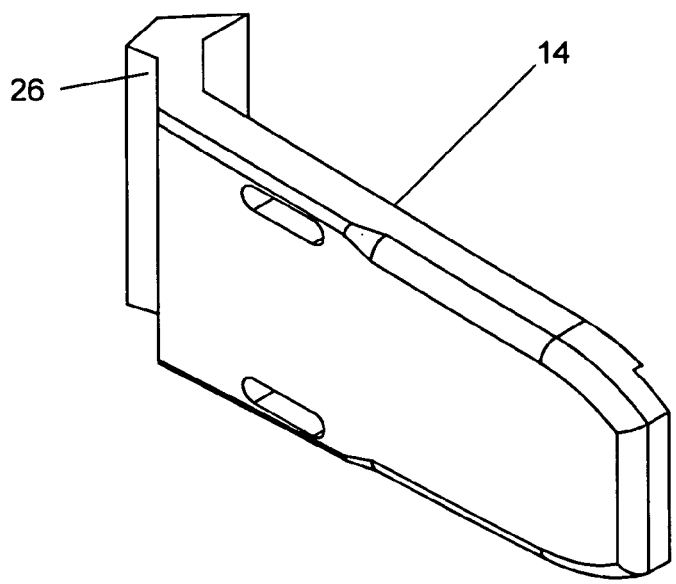
FIG. 2B is a perspective view of the wedge shown in FIG. 2A.

In the illustrated embodiment, the sensor 12 is carried by a wedge 14 or shoe that is positioned adjacent to the surface of the structure 16. The wedge 14 typically includes an angled surface that is positioned adjacent to the structure 16, such that the wedge and sensor 12 are oriented at an angle. This configuration facilitates the transmission of a shear wave 20 within the structure 16, while a mirror 26 reflects portions of the shear wave back to the sensor 12 for comparison with a return signal to determine if the gain of the sensor requires adjustment to compensate for any attenuation. Therefore, the sensor 12 can be moved manually along the structure 16 with the wedge 14 to inspect for a flaw 18. As shown in FIGS. 2A and 2B, the sensor 12 and wedge 14 may be hand-held, although the inspection system 10 is capable of being semi-automated or automated, such as by employing a scanner. Although not shown, the inspection system 10 may also include means for determining the position of the sensor 12 such that the data acquisition system can correlate the return signals with a position upon the structure 16. Further, the sensor 12 is generally capable of moving over a smooth, relatively rough, complex, and/or contoured surface while maintaining the desired orientation and proximity with the structure 16 to transmit a shear wave 20 towards or within the structure. Although the sensor 12 of the illustrated embodiment is carried by a wedge 14, the sensor may, instead, be carried by and positioned relative to the structure in other manners.

As shown in FIG. 1, the shear wave 20 is transmitted towards the surface of the structure 16, where the structure includes a coating 17 on one surface, i.e., its upper surface. A portion of the shear wave, i.e., an interrogating beam 22, travels through the coating 17 and within the structure. The interrogating beam 22 reflects one or more times between the opposed surfaces of the structure until the interrogating beam reaches a flaw 18. For instance, the interrogating beam 22 shown in FIG. 1 reflects off of opposing surfaces within the structure 16 nine times before reaching the flaw 18. The flaw 18 reflects the interrogating beam 22 back along the same path, or a substantially identical path, to the sensor 12. Based on the return signal associated with the interrogating beam 22 that is returned to the sensor 12 (e.g., amplitude, phase, etc.), the data acquisition system is capable of generating information to characterize the flaw 18 as known to those skilled in the art. For example, U.S. Pat. No. 6,848,312 to Georgeson, which is assigned to the present assignee and incorporated herein by reference, discloses an exemplary system for characterizing a flaw.

However, as described above, the presence of the coating 17 typically attenuates the strength of the signal of the interrogating beam 22, which may distort the signal or otherwise limit the effectiveness of characterizing the flaw 18. Therefore, in order to account for the attenuation caused by the coating 17, a reference beam 24 is employed. As the sensor 12 transmits the shear wave 20 towards the surface of the structure 16, a portion of the shear wave (i.e., a reference beam 24) reflects off of the surface, while the remaining portion of the shear wave (i.e., the interrogating beam 22) transmits through the coating 17 and into the structure 16.

The wedge 14 includes an ultrasonic mirror 26 that is positioned perpendicular, or approximately perpendicular to, the reflected reference beam 24. The mirror 26 reflects the reference beam 24 back to the sensor 12. More specifically, the first reflected reference beam 24 would reflect off of the mirror 26, off of the coating 17 again, and back to the sensor 12. In addition to the reference beam 24 that reflects off of the coating 17 without propagating through the structure 16, other reference beams may be created downstream by the refraction of the interrogating beam 22 at the interface defined by the coating. In the particular embodiment of the present invention shown in FIG. 1, there are a total of four reference beams 24. The second, third, and fourth reference beams 24 would also reflect off of the mirror 26, but would reflect from the mirror, into the structure 16, and then follow a zigzag path back to the sensor 12. Thus, a stronger signal of the reference beams 24 follow a zigzag path back to the sensor 12 (i.e., reflect between the opposing surfaces within the structure 16) when returning to the sensor, while only a portion of the remaining weaker signal of the reference beam reflects off of the surface of the structure. The number of reference beams 24 may be tailored based on shear angles and the size of the mirror 26, among other parameters.

Therefore, the sensor 12 is capable of acquiring attenuation information based on the peak signals associated with the reference beams 24. For example, signals 27 shown in FIG. 1 illustrate four return signals associated with respective reference beams 24 These signals, due to increased path length in the wedge 14, appear behind the signal of interest from the interrogating beam 22 and do not interfere with the interpretation the return signals. Based on the attenuation information and comparison between the return signals associated with each of the interrogating 22 and reference 24 beams, the gain of the sensor 12 is adjusted to compensate for the attenuation such that the return signal associated with the interrogating beam may be more accurately analyzed to characterize a flaw.

The general location of a flaw 18 may be predicted before inspecting the structure 16. For example, cracks typically develop proximate to a lower row of rivets in a lap joint (see range 30 in FIG. 1), scribe line cracks, as represented by flaw 18 in FIG. 1, develop proximate to lap splices (see range 32 in FIG. 1), and cracks develop proximate to reinforcing tear straps. Thus, at least those areas within the structure that are prone to developing flaws are inspected, and the sensor 12 is positioned within these areas to locate and characterize potential flaws. Typically, when the return signal associated with the interrogating beam 22 detected by the sensor 12 reaches a specific signal threshold, the presence of a flaw 18 is indicated and an alarm may be triggered to signify that a flaw is present. Thus, various audible or visual signifiers may be employed to indicate the presence of a non-negligible flaw.

Thus, the sensor 12 is typically in communication with a data acquisition system to process the data accumulated by the sensor and to display and/or store the processed data. In many cases, communications cable(s) 34 transmit data between the sensor 12 and the data acquisition system. In other embodiments, the data may be transmitted between the sensor 12 and the data acquisition system via wireless communications. The sensor 12 may be directly connected to the data acquisition system, or indirectly connected, such as via a network. In further embodiments of the present invention the data acquisition system may be located proximate to the sensor 12, such that remote connections between the sensor and data acquisition system are not necessary. Moreover, it is understood that data acquisition system could be incorporated with the sensor 12 such that the data is collected and processed by the sensor.

The data acquisition system typically includes a processor or similar computing device operating under the control of imaging software so that any attenuation caused by the coating 17 may be taken into account before identifying defects in the structure 16 that may be presented on a display. The processor could be embodied by a computer such as a desktop, laptop, or portable processing device capable of processing the data generated by the sensor 12 and creating an image of the scanned data that is shown on a display such as a monitor or other viewing device. The data acquisition system oftentimes generates images of the data and may also allow a user to store and edit previously created images. Therefore, a permanent record of the images may be kept for future use or record keeping. However, it is understood that the data acquisition system need not generate images, as the data acquisition system could mathematically collect and analyze data that a technician could use to characterize and locate a flaw based on the data.

Figure 3A:
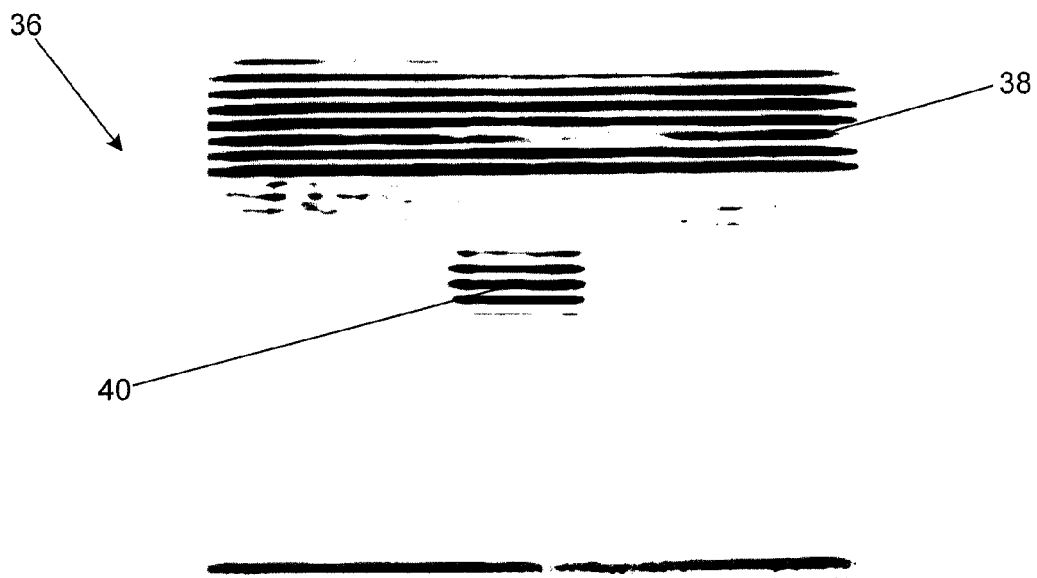
FIG. 3A is an image of a portion of an uncoated structure generated by a data acquisition system according to one embodiment of the present invention.

The data acquisition system of one embodiment is capable of generating various images, including A-scan, B-scan, and C-scan images of structures 16 based on data collected by the sensor 12. The images may include, among other information, data regarding defects, irregularities, or other imperfections in the structure 16. For example, FIG. 3A illustrates an image 36 of an uncoated structure 16 generated by a data acquisition system. The image 36 depicts mirror signals 38 associated with the reference beams 24 on a bare aluminum structure 16 (i.e., no coating). Signals 40 associated with the interrogating beam 22 represent an A notch for a NDT3065 testing standard, as known to those of ordinary skill in the art. Testing on bare aluminum is used to generate a calibration standard.

Figure 3B:
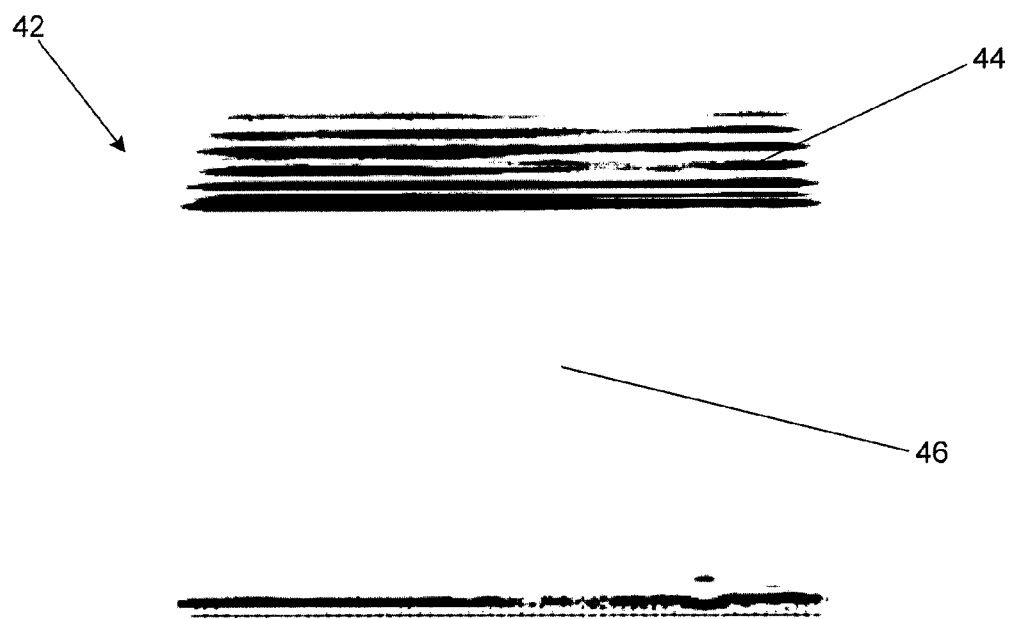
FIG. 3B is an image of a portion of a coated structure generated by a data acquisition system according to another embodiment of the present invention.

FIG. 3B illustrates an image 42 including mirror signals 44 from a structure 16 having the same A notch for the NDT3065 testing standard, but with a 5.4 mil coating. The signals 46 associated with the interrogating beam 24 demonstrate that the A notch for the same NDT3065 testing standard is not visible. Therefore, it is evident that the coating 17 on the structure 16 attenuated the signals 46 associated with the interrogating beam 22. Accordingly, the mirror signals 44 may then be compared to the mirror signals 38 acquired from the bare aluminum, and the gain of the sensor 12 can be adjusted to compensate for the attenuation so that the notch is more visible. In this regard, the mirror signals 44 from one coated structure have a smaller amplitude than the mirror signals 38 from the bare structure, thereby indicating that the return signals associated with the interrogating beam 24 that propagated through the coated structure must be amplified to provide the same level of visibility to the flaw as the return signals from a bare structure. While the extent of amplification of the interrogating beam 24 may be defined in various manners, the system and method of one embodiment amplify the interrogating signals in proportion to the amount by which the mirror signals from the uncoated structure exceed the mirror signals from the coated structure formed of the same material. For example, if the mirror signals from a coated structure decreased by 20% over the mirror signals from an uncoated structure, then the return signals from the interrogating beams that return from a coated structure may similarly be amplified by 20% to avoid being lost or filtered out as noise.

Figure 4A:
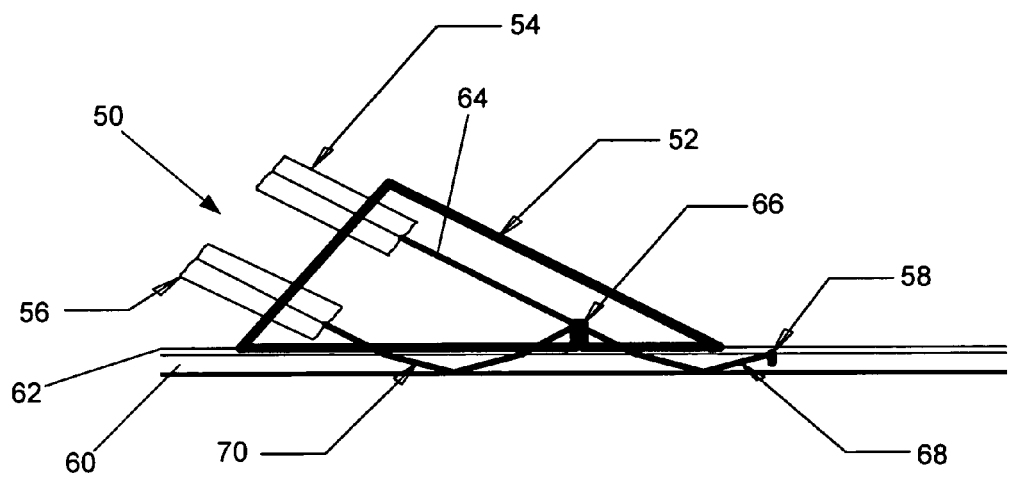
FIG. 4A is an elevation view of an inspection system including a wedge and a beam splitter according to another embodiment of the present invention.

It is understood that the inspection system 10 shown in FIGS. 1, 2A, and 2B may have various configurations for inspecting thin metallic structures 16 having a coating applied thereon. For example, FIG. 4A illustrates an inspection system 50 according to another embodiment of the present invention. The inspection system 50 includes a wedge 52 and a pair of ultrasonic sensors 54 and 56. The inspection system 50 is also capable of characterizing a flaw 58 within a structure 60 having a coating 62 applied to an upper surface thereof. Similar to that described above with respect to FIG. 1, a sensor 54 transmits a shear wave 64 towards the surface of the structure 16. However, a beam splitter 66 is employed to split the shear wave 64 into an interrogating beam 68 and a reference beam 70 before the shear wave reaches the surface of the structure 60. The interrogating beam 68 travels through the coating 62 and into the structure 60, reflects off of the opposite surface of the structure, and travels to the flaw 58. The flaw 58 reflects at least a portion of the interrogating beam 68 back to the sensor 54 along the same path that it traveled to the flaw. In addition, the reference beam 70 also travels through the coating 62 and within the structure, reflects off the opposite surface of the structure 60, and is received at the sensor 56. Thus, the sensor 54 acts as a pulse-echo sensor with respect to the interrogating beam 68, while the cooperation of sensors 54 and 56 act as pitch-catch sensors with respect to the reference beam 70.

Figure 4B:
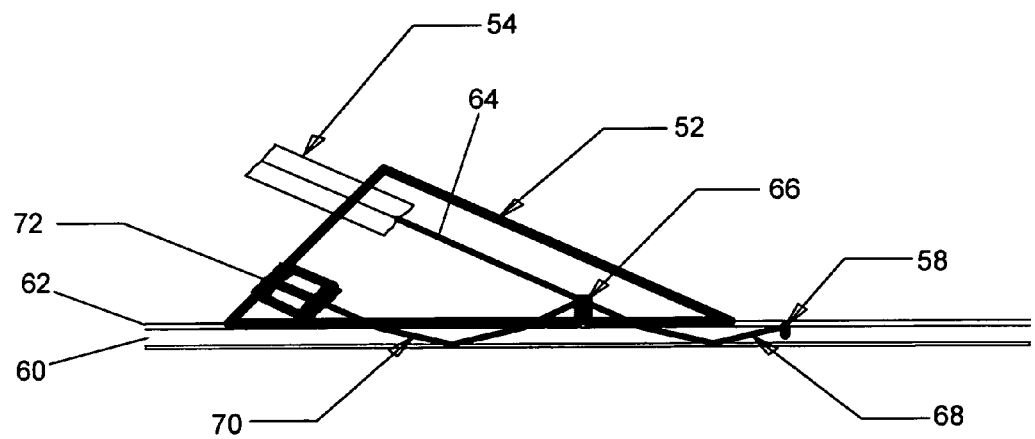
FIG. 4B is an elevation view of an inspection system including a wedge and a beam splitter according to yet another embodiment of the present invention.

FIG. 4B depicts a variation of the inspection system 50 shown in FIG. 3, where the sensor 56 is replaced with a reflector 72. The reflector 72 reflects the reference beam 70 back along the same path that it traveled from the beam splitter 66. Therefore, the sensor 54 is a pulse-echo sensor with respect to both of the interrogating 68 and reference 70 beams.

The inspection system 50 shown in FIGS. 4A and 4B is capable of being employed as a hand-held inspection system but may be used in a linear array transducer or in an automated or semi-automated system (e.g., a scanner). Typically, the signals associated with each of the interrogating 68 and reference 70 beams are subtracted or otherwise manipulated to determine the attenuation caused by the coating 62. Preferably, this calibration is only necessary during initial development to assign index numbers based on integration, beat pattern, or amplitude of the mirror signal pattern. The mirror signals from a coated inspection test piece then yield a similar index number. The gain of the sensor 54 could then be adjusted based on the index number to compensate for the coating attenuation so that the data acquisition system may properly characterize the flaw. Compensation, based upon predefined calibration standards, could occur in real time as a background operation for obtaining accurate flaw characterization without user intervention.

Figure 5:
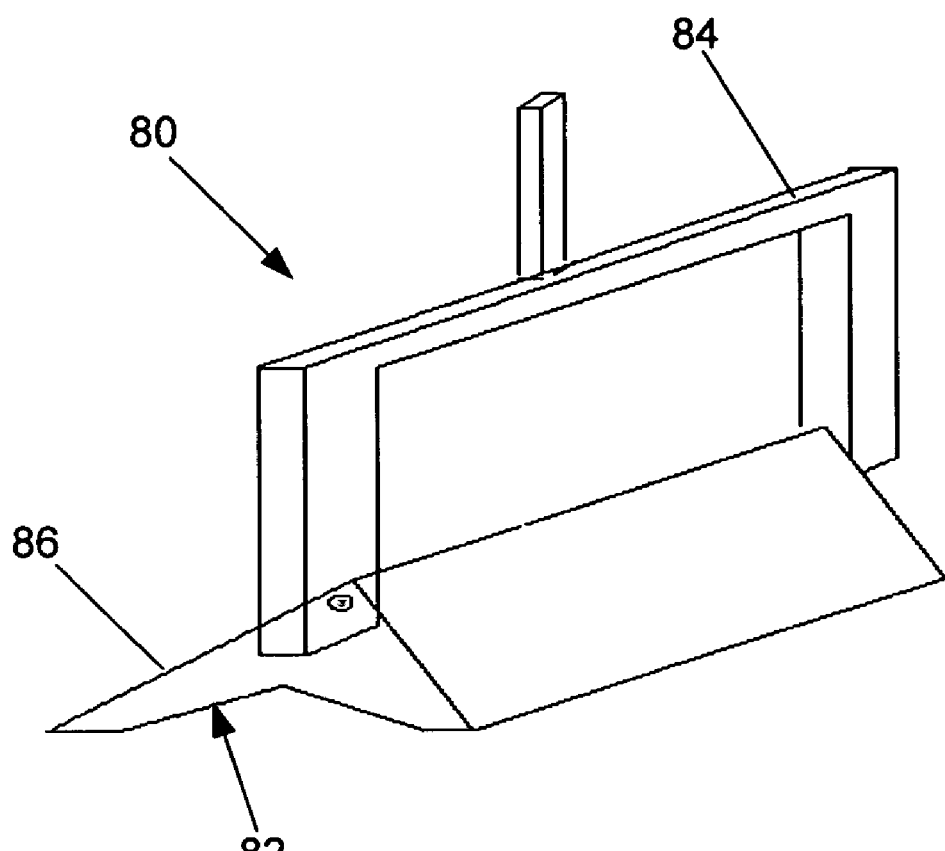
FIG. 5 is a perspective view of an inspection system including a tuning fork and ultrasonic mirror according to one embodiment of the present invention.

A further embodiment of an inspection system 80 according to the present invention is shown in FIG. 5. The inspection system 80 includes a wedge 82 attached to a tuning fork 84. The wedge 82 is placed proximate to a sensor or array of sensors such that a mirror 86 positioned on a surface of the wedge is positioned perpendicular, or substantially perpendicular, to the angle defined between the interrogating beam traveling within the structure and a reflected reference beam. The sensor is positioned adjacent to the wedge 82 such that the shear wave travels through the wedge and contacts the coated surface of the structure. As such, the shear wave is divided into an interrogating beam and a reference beam when the shear wave is refracted by the coated surface of the structure. The reference beam reflects off of the back surface of the structure, enters the wedge through the front surface of the coating, and reflects off of the mirror and back along its same path to the sensor. As before, the signal associated with the reference beam is utilized to determine the coating attenuation and thereby adjust the gain of the sensor to ensure that the characterization of the flaw is reliable. For example, calibration standards of known coating thickness may be used to compare the signal associated with the reference beam to determine the resulting adjustment of gain to compensate for the attenuation. Preferably, calibration is only necessary during initial development to assign index numbers based on integration, beat pattern, or amplitude of the mirror signal pattern. The mirror signals from a coated inspection test piece then yield a similar index number. The index number is used to determine the gain compensation.

Figure 6:
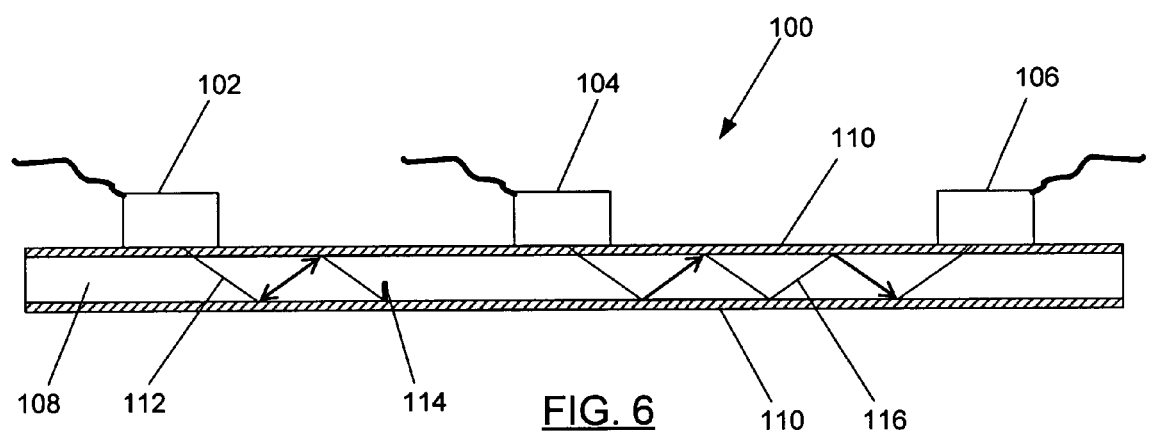
FIG. 6 is an elevation view of an inspection system including interrogating and reference ultrasonic sensors according to another embodiment of the present invention.

Another embodiment of the present invention is shown in FIG. 6. The inspection system 100 includes an interrogating sensor 102 and reference sensors 104 and 106. The sensors are employed to inspect the structure 108 having a coating 110 on its upper and lower surfaces. The interrogating sensor 102 is typically a pulse-echo ultrasonic transducer that transmits a shear wave 112 within the structure. The shear wave 112 reflects between the surfaces within the structure until the wave reaches a flaw 114. The flaw 114 reflects the shear wave back along its original path to the sensor 102.

The reference sensors 104 and 106 are typically pitch-catch ultrasonic sensors such that the sensor 104 transmits a shear wave 116 within the structure 108, while the sensor 106 receives the shear wave. Thus, the shear wave 112 transmitted by the interrogating sensor 102 travels an out-and-back path, while the shear wave 116 transmitted by the reference sensor 104 travels a one-way path to the receiving sensor 106. In the particular embodiment of the present invention shown in FIG. 6, each of the shear waves 112 and 116 reflects five times off of the opposing surfaces of the structure 108 and through the coating 110 twice. However, the shear waves 112 and 116 could reflect any number of times within the structure 108 depending on the number of signals or level of detail of inspection desired.

Each of the interrogating sensor 102 and reference sensor 104 transmit a respective shear wave 112 and 116 at substantially the same, frequency and angle within the structure 108 to ensure that the shear waves follow substantially similar paths. Moreover, because the general proximity of a potential flaw is typically known before inspecting the structure, the reference sensors 104 and 106 are positioned approximately twice the distance between the interrogating sensor 102 and the flaw 114 so that the path length between transmission and reception is about equal. Consequently, the signals associated with each of the shear waves 112 and 116 may be compared so that the coating attenuation may be taken into account and the gain of the interrogating sensor 102 properly adjusted to accurately characterize a flaw 114.

Therefore, it is apparent that the inspection systems 10, 50, 80, and 100 may have various configurations for obtaining attenuation information for a coated structure. For example, various devices (i.e., a wedges 14 and 52, tuning fork 80, or similar device) may be used to carry or position an ultrasonic sensor to direct or reflect an interrogating and/or reference beam within and/or off of a structure. Furthermore, the ultrasonic sensor could be directly attached or otherwise carried by the device, or positioned proximate to the wedge and still be capable of transmitting a shear wave towards and within a structure. In addition, various techniques may be employed to generate a reference beam and interrogating beam from a single shear wave, and each of the beams may reflect any number of times off of the coating or between opposing surfaces within the structure depending on the level of detail or type of flaws desired to be inspected. Similarly, the ultrasonic sensors may transmit shear waves at various frequencies and amplitudes to balance robustness and sensitivity of the inspection system, while the shear waves could be transmitted at various angles towards or within the structure.

Figure 7:
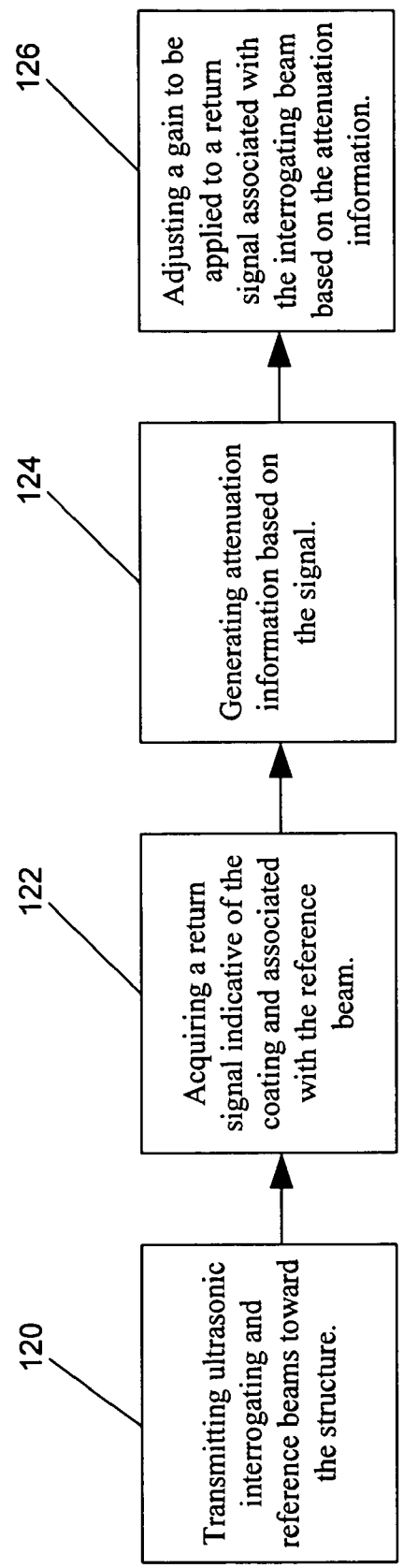
FIG. 7 is a flowchart depicting a method for inspecting a thin metallic structure having a coating applied thereon according to one embodiment of the present invention.

The flowchart of FIG. 7 depicts the general steps involved in inspecting a structure having a coating on one or more surfaces. The method includes transmitting at least a portion of an interrogating beam and a reference beam towards a structure (block 120). One or more return signals are acquired that are indicative of the coating and associated with the reference beam (block 122). Attenuation information is generated based on the acquired return signal(s) (block 124), and a gain to be applied to one or more return signals associated within the interrogating beam is adjusted based on the attenuation information (block 126).

Embodiments of the present invention provide several advantages. For instance, the inspection system is more reliable than conventional inspection techniques for inspecting thin metallic structures having a coating. By taking into consideration attenuation information caused by the coating, various types of defects that would potentially be undetected are properly characterized. Thus, the inspection system is capable of compensating for attenuation and adjusting the gain of an ultrasonic sensor to compensate for a coating present on the structure such that the inspection system is more reliable than inspection systems not taking into account the attenuation or overcompensating for the attenuation. In addition, the inspection system is more economical and efficient than conventional techniques where stripping of the coating is required.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for inspecting a structure having a coating on at least one surface comprising:
    at least one ultrasonic sensor positioned proximate to the structure, each sensor configured to transmit a shear wave toward the structure and receive return signals in response thereto, wherein the shear wave comprises at least one reference beam and at least one interrogating beam; and
    a data acquisition system in communication with the sensor for generating information indicative of the coating based on at least one return signal associated with the reference beam, wherein the data acquisition system is configured to characterize an anomaly within the structure based on at least one return signal associated with the interrogating beam.

2. The system according to claim 1, further comprising a device positioned adjacent to the structure for orienting the shear wave generated by the sensor relative to the structure.

3. The system according to claim 2, wherein the device comprises a wedge having at least one angular surface, and wherein the angular surface is positioned adjacent to the structure.

4. The system according to claim 2, further comprising an array of ultrasonic sensors that are each capable of transmitting a shear wave toward the structure at an orientation defined by the device.

5. The system according to claim 2, wherein the device comprises an angled reflection mirror attached to a tuning fork.

6. The system according to claim 2, wherein the device comprises a beam splitter capable of splitting the shear wave into the reference beam and interrogating beam.

7. The system according to claim 1, further comprising a second ultrasonic sensor, the second sensor capable of receiving the at least one return signal associated with the reference beam.

8. The system according to claim 2, wherein the device comprises a mirror positioned substantially perpendicular to an angle defined between the interrogating beam and the reference beam.

9. The system according to claim 8, wherein the mirror is positioned to reflect the reference beam back to the sensor.

10. The system according to claim 1, wherein the data acquisition system is capable of generating attenuation information based on the at least one return signal associated with the reference beam.

11. The system according to claim 10, wherein the data acquisition system is capable of applying a gain to at least one return signal associated with the interrogating beam based on the attenuation information.

12. The system according to claim 1, wherein at least one interrogating sensor is positioned adjacent to the structure, and wherein the interrogating sensor is capable of transmitting at least a portion of an interrogating beam through the structure and receiving at least one return signal associated with the interrogating beam.

13. The system according to claim 12, wherein a plurality of reference sensors are positioned adjacent to the structure, and wherein the reference sensors comprise a transmitting sensor capable of transmitting at least a portion of a reference beam through the structure and a receiving sensor capable of receiving at least one return signal associated with the reference beam transmitted by the transmitting sensor.

14. The system according to claim 13, wherein the data acquisition system is capable of communicating with each of the interrogating and reference sensors such that the data acquisition system generates information indicative of the coating based on the return signal received by the receiving sensor.

15. The system according to claim 13, wherein an approximate location of an anomaly within the structure is known prior to transmitting the interrogation beam with the interrogating sensor, and wherein the transmitting sensor and the receiving sensor are separated by approximately twice a distance between the interrogating sensor and the anomaly located within the structure.

16. The system according to claim 13, wherein the interrogating and reference sensors are configured to transmit the interrogating and reference beams, respectively, that have a frequency and angle that are substantially the same.

17. A method for inspecting a structure having a coating on at least one surface comprising:
    transmitting at least at least one ultrasonic reference beam and at least one ultrasonic interrogating beam toward the structure;
    acquiring at least one return signal indicative of the coating and associated with the reference beam;
    generating attenuation information based on the signal associated with the reference beam; and
    adjusting a gain to be applied to at least one return signal associated with the interrogating beam based on the attenuation information.

18. The method according to claim 17, further comprising generating information indicative of at least a portion of the structure based on the at least one return signal associated with the interrogating beam, and characterizing the anomaly within the structure based on the at least one return signal associated with the interrogating beam. Pg.22

19. The method according to claim 17, wherein transmitting comprises separately transmitting each of the interrogating and reference beams with respective ultrasonic sensors.

20. The method according to claim 17, wherein transmitting comprises splitting a shear wave into the reference beam and interrogating beam.

21. The method according to claim 17, further comprising comparing the attenuation information to a calibration standard prior to adjusting the gain to be applied to the at least one return signal associated with the interrogating beam.

* * * * *